United States Patent [19]

Klepacki

[11] Patent Number: 4,470,809

[45] Date of Patent: Sep. 11, 1984

[54] ORTHODONTIC APPLIANCE

[76] Inventor: Frank H. Klepacki, 1501 Burr Ridge Club Dr., 6240 S. County Line Rd., Burr Ridge, Ill. 60521

[21] Appl. No.: 501,505

[22] Filed: Jun. 6, 1983

[51] Int. Cl.³ .............................................. A61C 7/00
[52] U.S. Cl. .......................................... 433/15; 433/9
[58] Field of Search ................................ 433/9, 10, 15

[56] References Cited

U.S. PATENT DOCUMENTS

| | | | |
|---|---|---|---|
| 3,303,565 | 2/1967 | Newman | 433/9 |
| 3,345,745 | 10/1967 | Muller | 433/9 |
| 3,464,114 | 9/1969 | Brader | 433/10 |
| 3,922,787 | 12/1975 | Fischer et al. | 32/14 A |
| 3,936,939 | 2/1976 | Faunce | 433/9 |
| 3,964,165 | 6/1976 | Stahl | 433/15 |
| 4,216,583 | 8/1980 | Reynolds | 433/9 |
| 4,299,569 | 11/1981 | Frantz | 433/8 |

Primary Examiner—Robert Peshock
Attorney, Agent, or Firm—Keil & Weinkauf

[57] ABSTRACT

An aesthetic orthodonic appliance comprised of a shell molded from a tooth colored material. The rear surface of the appliance substantially conforms to the front surface of the tooth and is bonded thereto. The front surface of the shell generally follows the contour of the tooth surface and aesthetically blends to meet the tooth surface. The shell has a horizontal slot for accommodating an archwire and two tubular apertures through the shell to receive a ligation wire.

5 Claims, 4 Drawing Figures

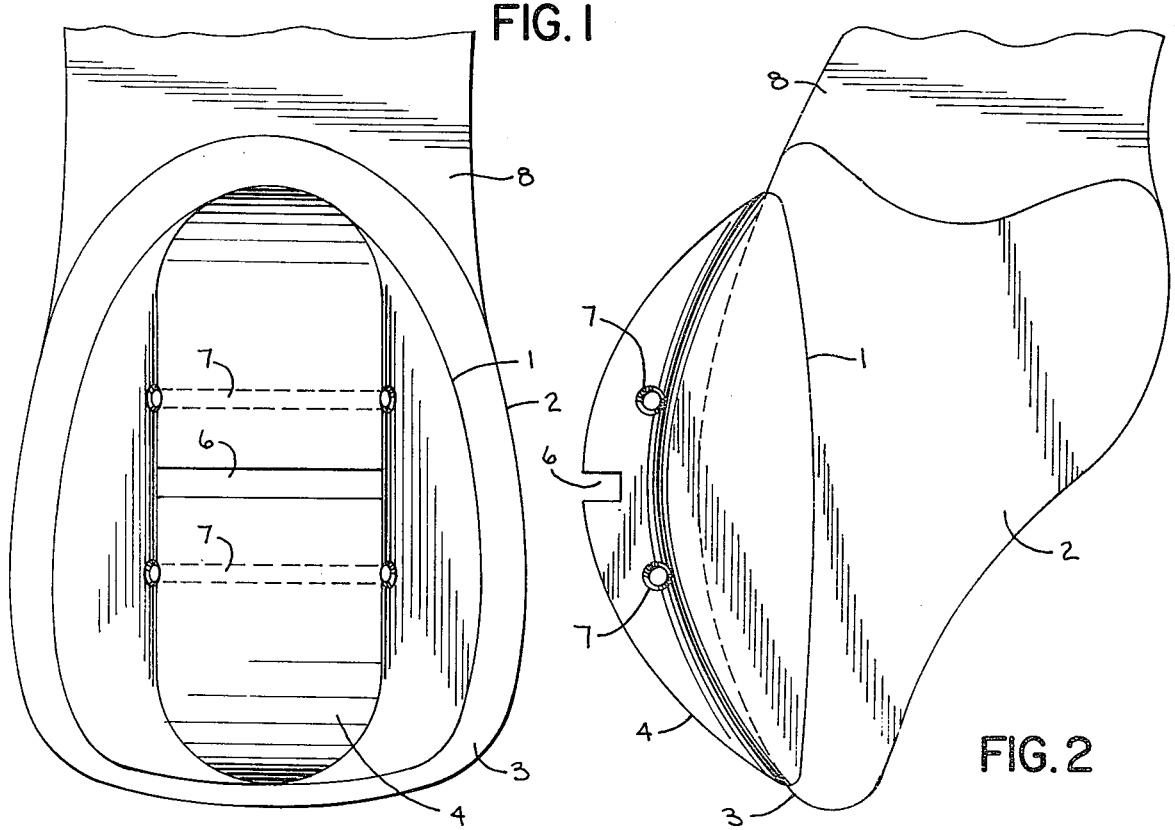
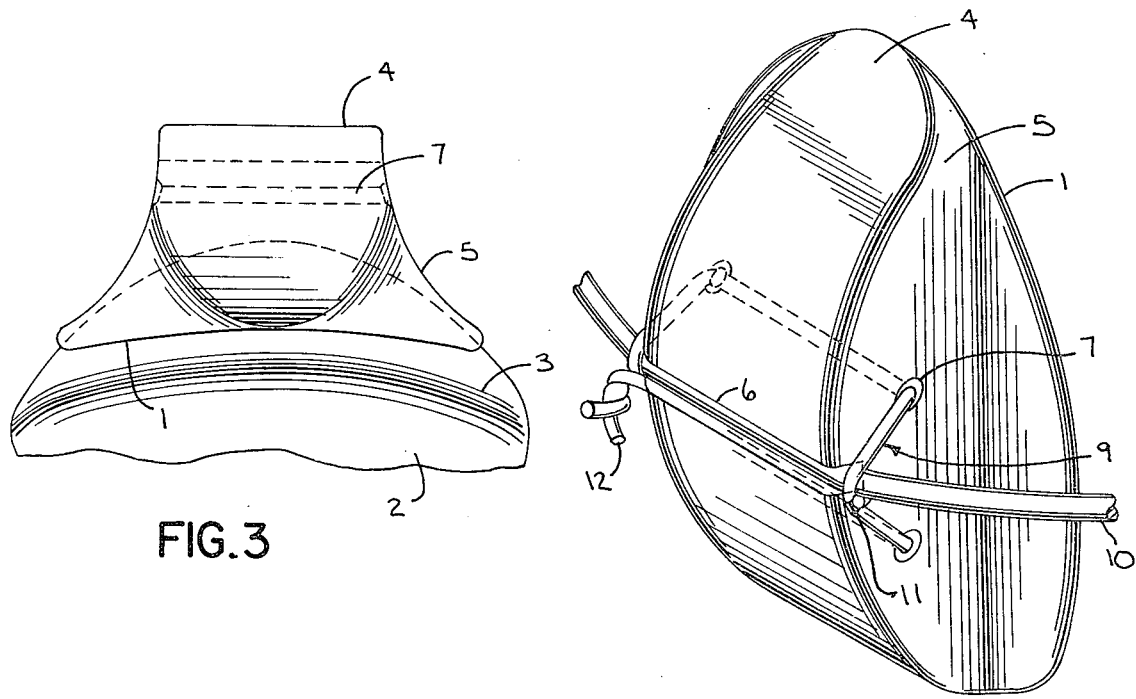

ORTHODONTIC APPLIANCE

FIELD OF INVENTION AND PRIOR ART

The present invention relates to orthodonic appliances, such as those permitting attachment of a brace in the form of a base wire or archwire thereto.

The placement of orthodonic braces on permanent teeth is more than fifty years old. The principal method of attaching the brace to the tooth was by use of a thin, flat, metal band that formed a ring around the entire tooth. Welded to the front surface of the band was a formed metal bracket.

The metals that were originally used for the bands and the brackets were various alloys of gold. In more recent years, gold was replaced by other alloys, chiefly stainless steel. All the various types of metal bands and brackets varied in color from light gold to gray steel—none was compatible with the color of natural teeth. The bands and brackets were attached to the teeth by cementing material, primarily oxyphosphate cement.

Later, a method of bonding orthodonic braces directly to the front surface of the teeth was developed. This bonding process eliminated the need for the band. Initally, all the bonding was done with metal brackets. The metal was still gray in color.

The metal brackets were made of cast or milled material and had very precise edges and some kind of double hook called a wing, compare for instance U.S. Pat. No. 4,216,583, which is used to ligate or hold an archwire in place. The wing projections can be irritating to the lips. In traumatic situations, severe laceration of the lips and cheeks can occur.

Soon, several plastic brackets appeared on the market. They were primarily shaped like the metal brackets, see for example U.S. Pat. No. 4,229,569, but they were essentially clear and transparent in color. The clear plastic eliminated the metallic appearance of the former brackets.

The original plastic brackets duplicated the size, shape and form of the metal brackets (U.S. Pat. No. 4,299,569). Due to the great reduction in strength of the plastic as compared to the metal, a high degree of fracture of the plastic brackets occurred. In order to reduce the breakage factor, the plastic brackets were changed by increasing their overall bulk. The net result was a plastic block or plug of material which was far from compatible with normal tooth contour. Numerous designs have been proposed for plastic orthodontic brackets, but most of the brackets have fallen into disuse. There are only three or four manufacturers that are offering a plastic bracket, while there are more than thirty manufacturers offering the metal brackets.

An attempt to improve earlier constructions of plastic brackets has been made in the design shown in U.S. Pat. No. 2,972,787. In this proposal, a somewhat more smoothly-shaped bracket body is used having the form of a triangle with one corner pointing in the direction of the biting edge of the tooth. A horizontal archwire slot is provided in the front of this triangular body and, peripherally around the entire base of the triangular bracket, an undercut or groove accommodating the ligation wire. This peripheral groove at the base, however, weakens the bracket so that the latter has to be given a greater thickness or cross section to provide the necessary amount of strength. In particular, the more space is allowed for the undercut to properly receive the ligation wire, the more the bulk of the bracket adjacent the biting edge of the tooth is increased. In the known design, the bracket is given the above-mentioned triangular shape to keep the greater shear forces due to the greater cross-sectional dimension from prying the bracket loose in response to mastication forces.

OBJECTS AND SUMMARY OF THE INVENTION

It is an object of the present invention to provide a safe orthodontic appliance, preferably of molded plastic material which, having all edges and corners removed, closely duplicates the front surface of the tooth and thereby becomes comparable in shape to a dental cap.

It is a specific object of the invention to provide a contoured bracket which avoids the above-mentioned shortcomings of the design disclosed in U.S. Pat. No. 3,922,787.

Briefly, these and other objects are met, according to the invention, by an orthodontic appliance which comprises a shell having a rear surface substantially conforming to the front face of a tooth for bonding said shell thereto, and having a front surface generally following the contour of, and blending into, the front face of the tooth, said front surface including a vertically extending central reinforcement portion having formed therein a substantially horizontally extending slot for accommodating an archwire and also two tubular apertures extending therethrough in substantially parallel relationship to said slot for receiving therein ligation wire means inserted laterally into said apertures.

In the embodiment of the invention disclosed hereafter, the shell is made from molded plastic material, with the color of the material closely matching the color of the tooth, thereby to further enhance the appearance of the appliance.

The unique design employing the two transverse tubular apertures results in a contour that is much thinner and more closely resembles the front surface of the tooth than was possible in the case of the prior art designs. This result is further enhanced by the fact that the two tubular apertures conceal the greater portion of the tie wire means and protect the mouth of the patient thereagainst. The shell according to the invention, provides for a substantial reduction in the shear forces on the bracket during chewing. This reduction of shear forces, moreover, reduces the possibility of failure or fracture of the bracket or of the cementing or bonding medium. The unique design of the contoured bracket of the invention also results in less irritation to the lips or cheeks. The absence of sharp edges virtually eliminates the possibility of traumatic perforation of the lip or cheek in case of an accidental blow. In addition, this unique contoured bracket or shell reduces crevices or areas where food might become entrapped, thereby allowing greater oral hygiene.

BRIEF DESCRIPTION OF THE DRAWING

A preferred embodiment of the invention will be described hereafter with reference to the accompanying drawing in which:

FIG. 1 is a frontal view of the orthodonic appliance according to the invention applied to the front of a tooth.

FIG. 2 is a side view of the orthodonic appliance as applied to the tooth.

FIG. 3 is an end view of the orthodonic appliance as applied to the tooth and as viewed from the biting edge thereof.

FIG. 4 is a perspective view, from the top right, of the orthodonic appliance as applied to the tooth, with the archwire and ligation wire in place.

DETAILED DESCRIPTION OF THE PREFERRED EMBODIMENT

In FIG. 1 of the drawing, the bracket or shell according to the invention has been designated as 2. Shell 2 is of molded plastic material, such as a polycarbonate plastic. The molded shell has a rear surface substantially conforming to the contour of the front face of tooth 1 of the patient, the tooth illustrated in the drawing being an upper incisor, by way of example. The rear surface of shell 2 is bonded to the front face of the tooth by a suitable, commercially-available bonding material. The color of the plastic material of the bracket or shell 2 is chosen so that it closely matches the natural color of tooth 1. Thus, the appliance according to the invention has a pleasant and inconspicuous appearance. The patient's gum is designed as 8 in the drawing.

The front surface of shell 2 generally follows the contour of the tooth and, throughout its periphery, blends into the surface of tooth 1, but it ends at a slight distance from the edge of the tooth, thereby leaving only a narrow peripheral portion 3 of the tooth uncovered.

The front surface of shell 2 includes a vertically-extending central reinforcement portion 4 to provide the necessary thickness for the formation therein of archwire slot 6 and two tubular apertures 7.

As shown in the drawing, reinforcement portion 4 blends smoothly into the remainder of the front face of the shell. Slot 6 is of rectangular cross section and it accommodates a base wire or archwire 10 which, as shown in FIG. 4, is of circular cross section. Archwire slot 6 may be beveled slightly to remove any sharp edges and allow for easy insertion of the archwire. The two tubular apertures 7 extend through reinforcement portion 4 in substantially parallel relationship to archwire slot 6. The tubular apertures 7 are designed to receive the leg portions of the generally U-shaped ligation wire 9 which, as shown in FIG. 4, is inserted laterally through apertures 7. The ends of tubular aperture 7 may be slightly countersunk to relieve stresses upon the ligation wire 9.

In the preferred embodiment, the two tubular apertures 7 through the reinforcement portion 4 are located above and below, respectively, of archwire slot 6 and slightly set back with respect to the bottom of this slot. With this arrangement, the bite end, that is the closed end 11, of the U-shaped ligation wire can be looped around the right end, as viewed in FIG. 4, of the archwire, the leg portions of the ligation wire can then be laterally inserted into the respective apertures 7 from that end, and the open ends 12 of the ligation wire, now protruding from that (left) end, bent upwards and twist-tied around this left end of the archwire. In this manner, both ends of archwire 10 are urged against the bottom of slot 6 with the twist-tied ends 12 of the ligation wire 9 providing the necessary urging force. Archwire 10 is thus safely "seated" in slot 6. U-shaped ligation wire 9, which when stretched out, may have an overall length of 2 to 2½ inches, preferably is made of flexible, non-tempered stainless steel, this being the usual material for orthodonic tie wires.

A preferred diameter for the ligation wire is 0.009 inch and for the tubular apertures 7 accommodating this wire about 0.012 inch.

In the preferred embodiment, shell 2 is concavely chamfered on the sides 5 of reinforcement portion 4 to facilitate removal of shell 2 from the tooth upon completion of the orthodonic treatment, by means of a tweezer-like plier. The chamfered sides 5 thus allow the vertically-extending central reinforcement portion 4 to be grasped by this tool. The necessity of contacting the enamel of the tooth at its periphery for the purpose of breaking the bond is thereby avoided.

The archwire slot preferably is 0.025 to 0.028 inch deep and 0.018 to 0.22 inch wide. Moreover, the archwire itself, rather than being round as shown herein, may have a rectangular or square cross section.

In conclusion it may be mentioned that slot 6 and tubular apertures 7 have been assumed herein to be machined into the shell after the molding thereof. However, slot 6 and, if special molds are used, apertures 7 could, alternatively, be integrally molded into the shell. As indicated above, shell 2 could also be made of other than plastic material, for instance cast metal could be used. It should be understood that the foregoing disclosure relates to only the preferred embodiment of the invention, and the claims are intended to cover all changes and modifications which do not constitute departures from the spirit and scope of the invention.

What is claimed is:

1. An orthodontic appliance comprising a shell having a rear surface substantially conforming to the front face of a tooth for bonding said shell thereto, and having a front surface generally following the contour of, and blending into, the front face of the tooth, said front surface including a vertically extending central reinforcement portion having formed therein a substantially horizontally extending slot for accommodating an archwire and also two tubular apertures extending therethrough in substantially parallel relationship to said slot for receiving therein ligation wire means inserted laterally into said apertures for engagement of said archwire, said apertures being provided in said central reinforcement portion in locations rearwardly of and adjacent to said slot such that said ligation wire means exert a substantial force on said archwire in a direction of the bottom of said slot, thereby to hold the archwire in place in said slot.

2. An orthodontic appliance as claimed in claim 1, wherein said tubular apertures are provided in said reinforcement portion in locations above and below said slot but slightly set back with respect to the bottom of said slot, said tubular apertures being arranged to receive leg portions of a U-shaped ligation wire such that said ligation wire, when inserted around the arch wire and into said apertures at one end and tied around the arch wire at the other end, urges the arch wire against the bottom of said slot.

3. An orthodontic appliance as claimed in claim 1, wherein the front surface of said shell is contoured to end throughout its periphery, at a slight distance from the tooth edges.

4. An orthodontic appliance as claimed in claim 1, wherein the central reinforcement portion, on its two sides is concavely chamfered to facilitate removal of the shell from the tooth.

5. An orthodontic appliance as claimed in claim 1, wherein said shell is molded of plastic, preferably tooth-colored, material.

* * * * *